United States Patent
Camborde et al.

(10) Patent No.: US 6,593,331 B2
(45) Date of Patent: Jul. 15, 2003

(54) METHOD FOR TREATMENT OF PAIN

(75) Inventors: Francoise Camborde, Orsay (FR); Alix Cloarec, Triel sur Seine (FR); Charles Conway, Cheshire, CT (US)

(73) Assignees: Laboratories UPSA (FR); Bristol-Myers Squibb Company, Princeton, NJ (US)

( * ) Notice: Subject to any disclaimer, the term of this patent is extended or adjusted under 35 U.S.C. 154(b) by 0 days.

(21) Appl. No.: 10/115,785

(22) Filed: Apr. 4, 2002

(65) Prior Publication Data

US 2002/0193380 A1 Dec. 19, 2002

Related U.S. Application Data

(60) Provisional application No. 60/284,425, filed on Apr. 17, 2001.

(51) Int. Cl.$^7$ ............... A61K 31/495; A61K 31/50; A61K 31/16
(52) U.S. Cl. .................. 514/252.18; 514/629
(58) Field of Search ............... 514/629, 252.18

(56) References Cited

U.S. PATENT DOCUMENTS

| 4,794,112 A | 12/1988 | Cooper |
| 6,150,365 A | 11/2000 | Mayol |

FOREIGN PATENT DOCUMENTS

| WO | WO 01/01989 | 1/2001 |

OTHER PUBLICATIONS

CA121:196575, Millan, Pain 1994 58(1) 45–61, abstract.*

The Pharmacologic Basis of Therapeutics, 5th edition, Macmillan Publishing Co., 1975, pp. 325–358.

Moltke, et al., "Gepirone and 1–(2–pyrimidinyl)–piperazine in vitro: human cytochromes mediating transformation and cytochrome inhibitors effects," Psychopharmacology, 1998, 140:293–299.

* cited by examiner

Primary Examiner—Rebecca Cook
(74) Attorney, Agent, or Firm—Richard P. Ryan

(57) ABSTRACT

A method of treating pain with acetaminophen comprises the concurrent administration of a hydroxyazapirone selected from 6-hydroxybuspirone or 3-hydroxygepirone. This combination of agents results in a more morphine-like analgesic response characterized by rapid onset and greater pain relief.

22 Claims, 2 Drawing Sheets

METHOD FOR TREATMENT OF PAIN

CROSS REFERENCE TO RELATED APPLICATION

This non-provisional application claims priority from provisional application U.S. Ser. No. 60/284,425 filed Apr. 17, 2001.

BACKGROUND OF THE INVENTION

This invention relates to the use of a therapeutic combination of nociceptive compounds to treat pain. The method of pain treatment comprises concurrent administration of a hydroxyazapirone selected from 6-hydroxybuspirone or 3-hydroxygepirone with acetaminophen (paracetamol). This combination of agents produces a more robust analgesic response with rapid onset.

Acetaminophen is an established analgesic agent having only weak anti-inflammatory activity and can be classified as a non-NSAID analgesic. Ibuprofen is an example of a non-steroidal analgesic having significant anti-inflammatory properties and is classified as a non-steroidal anti-inflammatory drug (NSAID). Acetaminophen is believed to relieve pain by elevation of the pain threshold and is generally given in amounts ranging from about 600 to 1300 mg per dose in humans.

While acetaminophen is equally effective as aspirin, it is unlikely to produce many of the adverse effects of aspirin and aspirin-containing products. Acetaminophen itself, however, has been associated with a propensity for contributing to liver damage in patients that ingest significant amounts of alcohol. The dose-related toxic effect of acetaminophen on liver is demonstrated by the hepatic toxicity seen with overdosage of acetaminophen. Therefore, it would be desirable to be able to effectively treat pain utilizing lower doses of acetaminophen.

Combinations of various analgesics to provide additive effects in treating pain are known in the literature; e.g., combinations of aspirin with codeine or other narcotic analgesics are known to provide additive analgesic effects in man. See: *The Pharmacologic Basis of Therapeutics*, $5^{th}$ edition, Macmillan Publishing Co., 1975, pp. 325–358. More active analgesic combinations are continually sought since they may be able to relieve pain with reduced dosages, thereby diminishing accompanying adverse effects and toxicities resulting from higher dosages. It is particularly desirable to discover an enhancing agent and/or a synergistic combination effect.

Acetaminophen analgesic combinations have been previously disclosed.

Cooper, in U.S. Pat. No. 4,794,112 disclosed combinations of hydroxyzine with acetaminophen as being effective analgesic compositions.

In our earlier disclosure, WO 01/01989, Cloarec, et al. described combinations of buspirone and acetaminophen (paracetamol) as being useful for treating pain. No reports of the use of other azapirones, e.g. gepirone in this regard have been reported.

Two hydroxyazapirones have been disclosed as metabolites of the azapirones buspirone and gepirone.

6-Hydroxybuspirone, chemically: 6-hydroxy-8-[4-[4-(2-pyrimidinyl)1-piperazinyl]butyl-8-azaspiro(4,5)-decane-7,9-dione is a metabolite of buspirone which was disclosed in U.S. Pat. No. 6,150,365 as being effective for the treatment of anxiety.

3-Hydroxygepirone, chemically: 4,4-dimethyl-3-hydroxy-1-[4-[4-(2-pyrimidinyl)1-piperazinyl]butyl-2,6-piperidinedione is a metabolite of gepirone reported by von Moltke, et al. in *Psychopharmacology*, 1998,140:293–299.

Neither 6-hydroxybuspirone nor 3-hydroxygepirone have been reported to possess antinociceptive effects. There has been no suggestion in the prior art to combine either of these compounds with acetaminophen to enhance its analgesic effect for the treatment of pain.

SUMMARY OF THE INVENTION

The present invention provides a method for treatment of pain comprising the concurrent administration of a hydroxyazapirone consisting of 6-hydroxybuspirone and 3-hydroxygepirone, and acetaminophen in a manner which results in strengthening of the antinociceptive effects of acetaminophen. The analgesia produced by the concurrent administration of acetaminophen and the hydroxyazapirone is more opioid-like, resembling morphine in having a more rapid onset and providing greater pain relief. The concurrent administration of 6-hydroxybuspirone or 3-hydroxygepirone also allows for the use of smaller amounts of acetaminophen, thereby reducing the liver toxicity potential. The present invention also comprises pharmaceutical compositions and pharmaceutical kit/packaging containing acetaminophen and 6-hydroxybuspirone or 3-hydroxygepirone for combination therapy.

BRIEF DESCRIPTION OF THE DRAWINGS

FIG. 1 6-Hydroxybuspirone (5 mg/kg; ip) strengthens the analgesic effect of acetaminophen (300 mg/kg; ip). The hindpaw thermal escape response of albino rats was elevated significantly above vehicle (saline+PETW ... Δ... ) by acetaminophen (Acet 300 mg/kg; ip —•—) alone or 6-hydroxybuspirone (6-OH-Busp 5 mg/kg; ip—□—) alone. When 6-hydroxybuspirone was co-administered with acetaminophen (6-OH-Busp+Acet, 5+300 mg/kg; ip—■—), a greater analgesic effect was observed at 60 to 120 min than either compound given alone. Data are expressed as mean±sem (n=5–8 rats per group). *$p<0.05$**$p<0.01$ 6-OH-Busp+Acet compared to vehicle (saline+PETW). +$p<0.05$++$p<0.01$ Acet compared to saline+PETW. †$p<0.05$††$p<0.01$ 6-OH-Busp compared to saline+PETW.

DETAILED DESCRIPTION OF THE INVENTION

Figure 1:
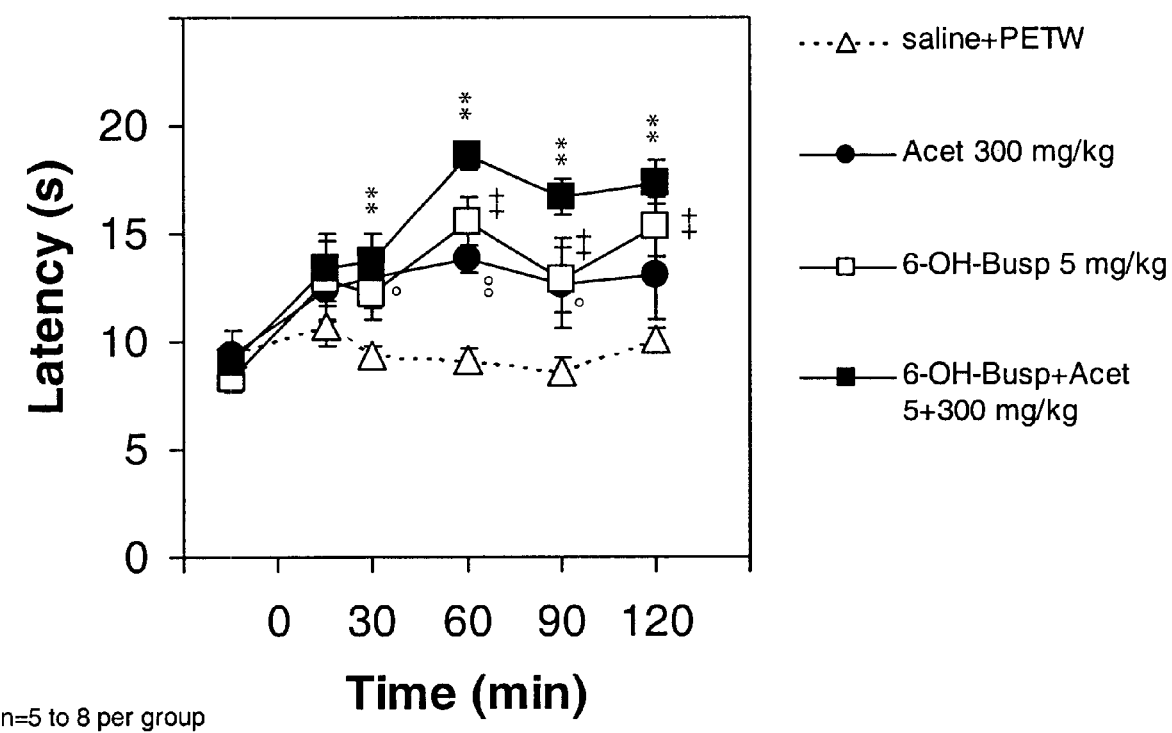

In accordance with the present invention, a greater measure of pain relief in mammals is achieved by concurrent systemic administration of acetaminophen and a hydroxylated azapirone (6-hydroxybuspirone or 3-hydroxygepirone) or an acid salt form thereof in an amount sufficient to strengthen the analgesic activity of the acetaminophen with the total amount of acetaminophen and hydroxyazapirone to be administered is an amount sufficient to relieve pain in the mammal. While the hydroxyazapirone may be selected from 6-hydroxybuspirone or 3-hydroxygepirone;

6-hydroxybuspirone is most preferred and will be used as the exemplary hydroxyazapirone in describing the present invention.

The concurrent addition of either of the hydroxyazapirones to acetaminophen administration has been found to produce a marked enhancement of acetaminophen's analgesic effects. This combination therapy employing either hydroxyazapirone with acetaminophen results in an enhanced onset of therapeutic effect and greater efficacy compared to acetaminophen alone. By strengthening acetaminophen's analgesic effects, lower doses of acetaminophen can be employed, thereby limiting the potential for adverse effects. Moreover, acetaminophen enhanced with either of the hydroxyazapirones can be used to treat severe pain for which acetaminophen alone might not provide sufficient relief. Thus, this method of pain treatment would widen the use of acetaminophen to treat pain of varied origins in a much larger number of patients. The present method of pain treatment is also intended for application to animals.

"Concurrent administration", "administered in combination" or similar phrases referring to the acetaminophen and hydroxyazapirone components mean that the components are administered concurrently to the mammal being treated. By "concurrently," it is meant that each component may be administered at the same time or sequentially in any order at different points in time. However, if not administered at the same time, they should be administered sufficiently closely in time so as to provide the desired enhancement of treatment effect. Suitable dosing intervals and the order of administration with such compounds will be readily apparent to those skilled in the art, once armed with the present disclosure. Preferably both components are administered at the same time or within the same hour.

As used herein, the term "animal" shall refer to a vertebrate animal. More preferably, the vertebrate animal is a mammal. As used herein, the term "mammal" shall refer to the Mammalia class of higher vertebrates. The term "mammal" includes, but is not limited to, a human. The term "treating" as used herein includes prophylaxis of the named condition or amelioration or elimination of the condition and/or its characteristic symptoms once it has been established.

As used herein, the term "pain" shall refer to all types of pain. Preferably, the term shall refer to acute and chronic pains, such as neuropathic pain and post-operative pain, chronic lower back pain, cluster headaches, herpes neuralgia, phantom limb pain, central pain, dental pain, opioid-resistant pain, visceral pain, surgical pain, bone injury pain, pain during labor and delivery, pain resulting from burns, including sunburn, post partum pain, migraine, angina pain, and genitourinary tract-related pain including cystitis, the term shall also preferredly refer to nociceptive pain or nociception.

By "therapeutically effective amount" is meant an amount of acetaminophen that when administered alone is at least minimally effective in providing pain relief.

By "pain-relief enhancing amount" is meant an amount of the hydroxyazapirone that significantly strengthens the analgesic effect and quickens the onset of action.

Acid addition salts of the hydroxyazapirones are obtained by methods known in the art and can encompass a reaction of 3-hydroxygepirone or 6-hydroxybuspirone with an organic or inorganic acid, preferably by contact in solution. Examples of useful organic acids are carboxylic acids such as maleic acid, acetic acid, tartaric acid, propionic acid, fumaric acid, isethionic acid, succinic acid, pamoic acid, and the like; useful inorganic acids are hydrohalide acids such as HCl, HBr, HI; sulfuric acid; phosphoric acid; and the like. HCl acid salt of the hydroxyazapirones are preferred.

Both of the azapirone agents utilized in the present method of treating pain contain an asymmetric carbon at the site of attachment of the hydroxy group; i.e., at the 3-position of the gepirone molecule and the 6-position of the buspirone molecule. This results in optical stereoisomerism giving rise to the presence of two enantiomers for each hydroxyazapirone.

The concurrent administration of the hydroxyazapirone agent contemplates use of both racemic and individual enantiomer forms of 6-hydroxybuspirone and 3-hydroxygepirone. The (R)- and (S)-enantiomers of 6-hydroxybuspirone and 3-hydroxygepirone may be prepared utilizing methods of synthesis and enantiomeric separation known to one skilled in the art. One method of preparation (Scheme 1) utilizes the parent azapirone (buspirone/gepirone) as a starting material to produce the racemic hydroxyazapirone product that is then separated into the two enantiomers by chiral chromatographic techniques.

Scheme 1

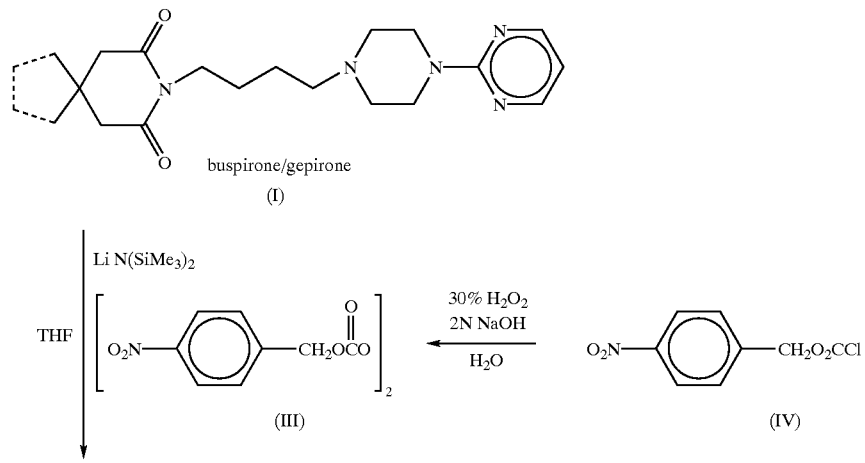

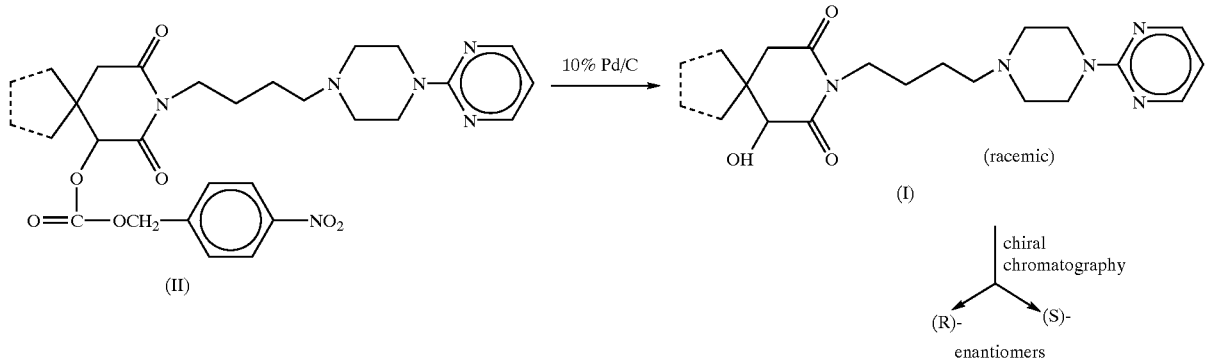

An improved one-step synthesis of racemic hydroxyazapirone is set forth in Scheme 2. Again, enantiomeric separation provides both the (R)- and (S)-isomers of the hydroxyazapirone.

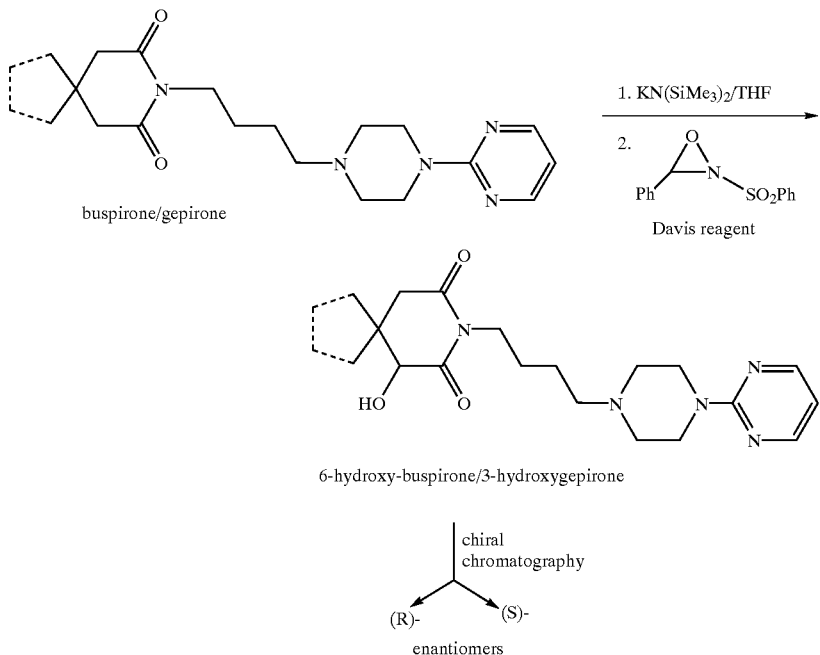

In addition to the use of racemic mixtures of the individual hydroxyazapirones, the present invention also encompasses the use of S-hydroxyazapirones, substantially free of R-hydroxyazapirones and R-hydroxyazapirones, substantially free of the S-isomer. The R- and S-isomers of the hydroxyazapirones may be resolved by methods known to those skilled in the art, for example by formation of diastereoisomeric salts or complexes which may be separated, for example, by crystallization; via formation of diastereoisomeric derivatives which may be separated, for example, by crystallization, gas-liquid or liquid chromatography; selective reaction of one enantiomer with an enantiomer-specific reagent, for example enzymatic oxidation or reduction, followed by separation of the modified and unmodified enantiomers; or gas-liquid or liquid chromatography in a chiral environment, for example on a chiral support, such as silica with a bound chiral ligand or in the presence of a chiral solvent. It will be appreciated that where the desired enantiomer is converted into another chemical entity by one of the separation procedures described above, a further step is required to liberate the desired enantiomeric form. Alternatively, specific enantiomer may be synthesized by asymmetric synthesis using optically active reagents, substrates, catalysts or solvents, or by converting an enantiomer to the other by asymmetric transformation.

The amounts of the hydroxyazapirone compound, 6-hydroxybuspirone or 3-hydroxygepirone or a salt form or hydrate thereof, as well as the dose of acetaminophen selected may depend on several variables. Similarly, dosage amounts of a pharmaceutical combination formulation having a fixed ratio of acetaminophen to the hydroxyazapirone compound would also have a dependency on these same factors. Some of these factors would be: route of administration, time of drug release (e.g., instant or extended), administration schedule, pain severity, age and condition of the patient, the patient's body weight, and the like. With respect to acetaminophen, it will be concurrently administered with an effective pain relieving enhancing amount of one of the hydroxyazapirones; e.g., 6-hydroxybuspirone (or its acid salts) in a total combined pain relieving amount, in doses given 1 to 6 times a day as needed to relieve pain. In general, it is desirable to employ at least an amount of acetaminophen that by itself would be minimally effective in producing analgesia. Suitable per dose amounts for acetaminophen are from 200 to 1300 mg, but are preferably from 300 to 650 mg.

In Table 1 are shown a general and preferred dose ranges of acetaminophen, hydroxyazapirone, and the weight ratio range.

TABLE 1

Acetaminophen-Hydroxyazapirone Dose Ranges

|  | Acetaminophen Dose Range | Hydroxyazapirone (HCl) Dose Range | Hydroxyazapirone: Acetaminophen Weight Ratio Range |
|---|---|---|---|
| General: | 200–1300 | 0.5–20 | 1:10 to 1:2600 |
| Particular: | 300–650 | 1.0–10 | 1:30 to 1:650 |
| More particular: | 300–500 | 3.0–8 | 1:40–1:150 |

The mechanism of action for pain relief enhancement of acetaminophen by the hydroxyazapirone compound is not well understood at this point but it does not appear to involve pharmacokinetic drug interaction effects. The hydroxyazapirone component is believed to elicit pharmacologic effects by virtue of acting as an agonist at 5-HT1A receptors, at least presynaptically. The azapirones themselves, such as buspirone or gepirone, are believed to act at agonists at presynaptic 5-HT1A receptors and as a partial agonist/antagonist at postsynaptic 5-HT1A receptors.

Acetaminophen is believed to act by elevating the pain threshold in patients.

Acetaminophen is generally given in analgesic doses ranging from about 300 to 1300 mg and preferably from about 650 to 1300 mg with a maximum recommended daily dose of about 4000 mg. For concurrent administration in the present method of pain treatment, acetaminophen doses would be no lower than the minimally effective dose (MED) for effective analgesia. It is expected that the hydroxyazapirone dose would generally be below 20 mg. There has been no clinical dose established for either of the hydroxyazapirone's use as a single agent to treat pain. The hydroxyazapirone compound is preferably employed in acid addition salt form; e.g., the hydrochloride salt.

Consequently, the weight ratio of acetaminophen to hydroxyazapirone, while selected to provide the highest level of pain relief enhancement, would be generally from about 10:1 to 2600:1 and particularly about 40:1 to 150:1.

The analgesic enhancement effect has been demonstrated in accepted rodent pain models.

Using a mouse hot plate test procedure described by Eddy, et al., in *J. Pharmacol. Exp. Ther.,* 1950, 98: 121–137; 6-hydroxybuspirone demonstrated potentiation of acetaminophen at a 6-hydroxybuspirone to acetaminophen weight ratios of 1:3, 1:10, and 1:30.

More definitive testing was done using the rat hindpaw thermal escape paradigm which is described in more detail infra. The results of these tests are displayed in FIGS. 1 to 2.

FIG. 1 demonstrates the analgesic enhancing effect of 5 mg/kg 6-hydroxybuspirone on a 300 mg/kg analgesic dose of acetaminophen.

Figure 2:
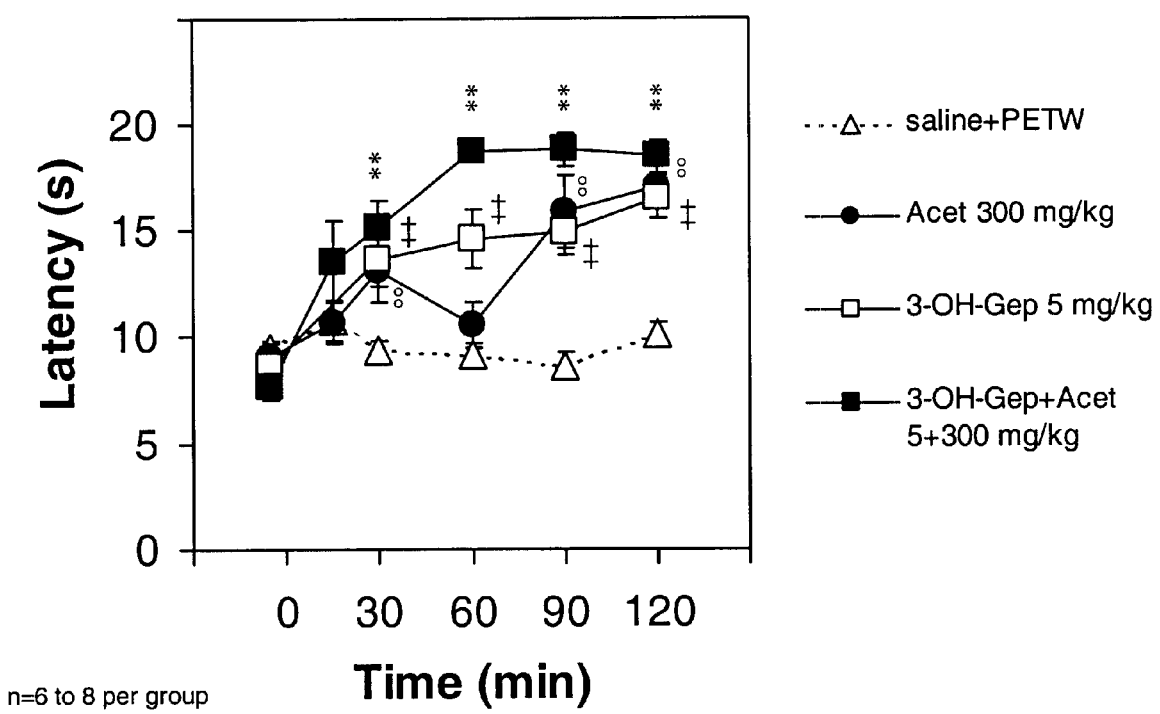
FIG. 2 Coadministration of 3-Hydroxygepirone (5 mg/kg; ip) and Acetaminophen (300 mg/kg; ip) produces faster onset peak analgesia compared to Acetaminophen alone. The hindpaw thermal escape latency of albino rats was elevated significantly above vehicle (saline+PETW ... Δ...) by acetaminophen (Acet 300 mg/kg; ip—•—) alone or by 3-hydroxygepirone (3-OH-Gep 5 mg/kg; ip—□—) alone, and peak analgesic effect was observed at 120 min post injection. When 3-hydroxygepirone was co-administered with acetaminophen (3-OH-Gep+Acet, 5+300 mg/kg; ip—■—) the peak analgesic effect was achieved earlier at 60 min post injection. Data are expressed as mean±sem (n=5–8 rats per group). *$p<0.05$**$p<0.01$ 3-OH-Gep+Acet compared to vehicle (saline+PETW). °$p<0.05$°°$p<0.01$ Acet compared to saline+PETW. †$p<0.05$††$p<0.01$ 3-OH-Gep compared to saline+PETW.

FIG. 2 demonstrates the analgesic enhancing effect in this model for 3-hydroxygepirone. The 300 mg/kg dose of acetaminophen combined with 5 mg/kg 3-hydroxygepirone demonstrates a more rapid onset of peak analgesic effect compared to either agent alone.

These data demonstrate that the concurrent administration of a potentiating amount of a hydroxyazapirone with a minimally effective acetaminophen dose results in analgesia which is faster in onset and more robust.

With regard to single agent or combined agent formulations of acetaminophen and hydroxyazapirone to be employed in the present method, considerable variation in formulations and components may be practiced without departing from the present invention. Any salt form of one of the two hydroxyazapirones having acceptable formulation properties can be used. However, the HCl salt form is preferred.

The present invention then comprises the concurrent administration of a therapeutically effective amount of acetaminophen and an analgesia-enhancing amount of a hydroxyazapirone selected from the group consisting of 6-hydroxybuspirone or 3-hydroxygepirone or one of its acceptable salts or hydrates.

The present invention also includes pharmaceutical combination compositions comprising the hydroxybuspirone and acetaminophen components. Such compositions may be in solid or liquid dosage units and may further include suitable pharmaceutical carriers and excipients.

The compositions of this invention may be suitable for administration to an animal. Such animals include both domestic animals; for example, livestock, laboratory animals and household pets, and non-domestic animals such as wildlife. More preferably, the animal is a vertebrate. Most preferably, a compound of this invention shall be administered to a mammal. It is especially preferred that the animal is a domestic mammal or a human. For such purposes, a compound of this invention may be administered as a feed additive.

The most preferred mammal is a human.

Pharmaceutical kit packaging is also envisioned for the present invention. In the kit package are provided both acetaminophen and buspirone unit dosage forms for use in the present method.

Dosage and Formulation

The hydroxyazapirone component and acetaminophen component combination treatment of the invention can be given via parenteral, rectal, buccal, transdermal, or, preferably, oral routes of administration by any conventional means available for the use in conjunction with pharmaceuticals, either as individual separate dosage units administered simultaneously or concurrently, or in a physical combination of each component therapeutic agent in a single or combined dosage unit. The active agents can be administered alone, but are generally administered with a pharmaceutical carrier selected on the basis of standard pharmaceutical practice.

In general, acetaminophen would be administered at levels in accordance with guidelines found in standard medical/drug references such as the *Physicians Desk Reference* and the like. This would be in the range of about 300 to 1300 mg per dose. Amounts of the hydroxyazapirone for concurrent administration would be in the range of from about 0.5 to 20 mg and preferably from 3 to 8 mg per dose.

The dosage administered will, of course, vary depending on the use and known factors such as the age, health, and weight of the recipient; nature and extent of symptoms, concurrent treatments, if any, frequency of treatment, and the effect desired. The recipient may be any type of mammal, but is preferably a human.

In the methods of the present invention, the two agents, hydroxyazapirone and acetaminophen form the active ingredients, and are typically administered in admixture with suitable pharmaceutical diluents, excipients, or carriers (collectively referred to herein as carrier materials) suitably selected with respect to the intended form of administration, that is, oral tablets, capsules, elixirs, syrups and the like, and consistent with conventional pharmaceutical practices.

For instance, for oral administration in the form of a tablet or capsule, the active drug component can be combined with an oral, non-toxic, pharmaceutically acceptable, inert carrier such as lactose, starch, sucrose, glucose, methyl cellulose, magnesium stearate, dicalcium phosphate, calcium sulfate, mannitol, sorbitol and the like; for oral administration in liquid form, the oral drug components can be combined with any oral, non-toxic, pharmaceutically acceptable inert carrier such as ethanol, glycerol, water, and the like. Moreover, when desired or necessary, suitable binders, lubricants, disintegrating agents, and coloring agents can also be incorporated into the mixture. Suitable binders include starch, gelatin, natural sugars such as glucose or beta-lactose, corn sweeteners, natural and synthetic gums such as acacia, tragacanth, or sodium alginate, carboxymethylcellulose, polyethylene glycol, waxes, and the like. Lubricants used in these dosage forms include sodium oleate, sodium stearate, magnesium stearate, and the like. Disintegrators include, without limitation, starch, methyl cellulose, agar, bentonite, xanthan gum, and the like.

Gelatin capsules contain the active ingredient and powdered carriers, such as lactose, starch, cellulose derivatives, magnesium stearate, stearic acid, and the like. Similar diluents can be used to make compressed tablets. Both tablets and capsules can be manufactured as sustained release products to provide for continuous release of medication over a period of hours. Compressed tablets can be sugar coated or film coated to mask any unpleasant taste and protect the tablet from the atmosphere, or enteric coated for selective disintegration in the gastrointestinal tract.

Liquid dosage forms for oral administration can contain coloring and flavoring to increase patient acceptance.

The combination products of this invention may be formulated such that, although the active ingredients are combined in a single dosage unit, the physical contact between the active ingredients is minimized. In order to minimize contact, for example, one or more of the active ingredients may be enteric coated. By enteric coating one of the active ingredients, it is possible not only to minimize the contact between the combined active ingredients, but also, it is possible to control the release of one of these components in the gastrointestinal tract such that one of these components is not released in the stomach but rather is released in the intestines. Another embodiment of this invention provides for a combination product wherein one or more of the active ingredients is coated with a sustained-release material which effects a sustained-release throughout the gastrointestinal tract and also serves to minimize physical contact between the combined active ingredients. Furthermore, the sustained-released component can be additionally enteric coated such that the release of this component occurs only in the intestine. Still another approach would involve the formulation of a combination product in which the one or more components is coated with a sustained and/or enteric release polymer, and the other(s) component is also coated with a polymar such as a low viscosity grade of hydroxypropyl methylcellulose or other appropriate materials as known in the art, in order to further separate the active components. The polymer coating serves to form an additional barrier to interaction with the other component.

Dosage forms of the combination products of the present invention wherein one active ingredient is enteric coated can be in the form of tablets such that the enteric coated component and the other active ingredients are blended together and then compressed into a tablet or such that the enteric coated component is compressed into one tablet layer and the other active ingredient is compressed into an additional layer. Optionally, in order to further separate the two layers, one or more placebo layers may be present such that the placebo layer is between the layers of active ingredients. In addition, dosage forms of the present invention can be in the form of capsules wherein one active ingredient is compressed into a tablet or in the form of a plurality of microtablets, particles, granules or non-perils, which are then enteric coated. These enteric coated microtablets, particles, granules or non-perils are then placed into a capsule or compressed into a capsule along with a granulation of the other active ingredient.

These as well as other ways of minimizing contact between the components of combination products of the present invention, whether administered in a single dosage form or administered in separate forms but at the same time or concurrently by the same manner, will be readily apparent to those skilled in the art, based on the present disclosure.

Specific Embodiments

The compounds whose use constitutes this invention and their methods of preparation will appear more fully in light of the following examples which are given for the purpose of illustration only and are not to be construed as limiting the invention in sphere or scope.

EXAMPLE 1

Preparation of 6-hydroxy-buspirone
A. Di-4-nitrobenzyl Peroxydicarbonate (III)

Di-4-nitrobenzyl peroxydicarbonate was prepared using a modification of the literature procedure[1]. Thus, to an ice-cold solution of 4-nitrobenzyl chloroformate (10.11 g, 4.7 mmol) in acetone (20 mL) was added dropwise over 30 min an ice-cold mixture of 30% $H_2O_2$ (2.7 mL, 24 mmol) and 2.35 N NaOH (20 mL, 47 mmol). The mixture was vigorously stirred for 15 min and then it was filtered and the filter-cake was washed with water and then with hexane. The resulting damp solid was taken up in dichloromethane, the solution was dried ($Na_2SO_4$) and then it was diluted with an equal volume of hexane. Concentration of this solution at 20° C. on a rotary evaptor gave a crystalline precipitate which was filtered, washed with hexane and dried in vacuo to give compound III (6.82 g, 74%) as pale yellow microcrystals, mp 104° C.(dec).
[1] F. Strain, et al., *J. Am. Chem. Soc.,* 1950, 72, 1254

Di-4-nitrobenzyl peroxydicarbonate was found to be a relatively stable material which decomposed as its melting point with slow gas evolution. In comparison, dibenzyl peroxydicarbonate[2] decomposed with a sudden vigorous expulsion of material from the melting point capillary.
[2] Cf. M. P. Gove. J. C. Vedaras, *J. Org. Chem.,* 1986, 51, 3700

B. 6-(4-Nitrobenzyl Peroxydicarbonatyl)-8-[4-[4-(2-pyrimidinyl)-piperazinyl]-butyl]-8-azaspiro[4.5]-7,9-dione (II).

To a solution of 8-[4-[4-(2-pyrimidinyl)-piperazinyl]-butyl]-8-azaspiro[4.5]-7,9-dione (buspirone: 10 g, 26 mmole) in dry THF (250 mL) was added LiN($Me_3Si$)$_2$ (28.5 mL of a 1 M THF solution) at 78° C. and stirred for 3 h and then a solution of di-4-nitrobenzyl peroxydicarbonate (11.2 g) in dry THF (150 mL) was added dropwide over 1 h. Stirring was continued at −78° C. for 1 h.

The cooling bath was removed and the reaction solution was poured into a mixture of $H_2O$ and EtOAc. The organic phase was separated and washed with $H_2O$ and then brine. The organic base was dried and then evaporated to a viscous oil. Flash chromatography of this oil, eluting the silica column with MeCN-EtOAc (1:2) gave crude product which was washed with acetone, to remove unreacted buspirone, leaving 6.23 g of a white solid (46%) product (II).

C. 6-Hydroxy-8-[4-[4-(2-pyrimidinyl)-piperazinyl]-butyl]-8-azaspiro[4.5]-7,9-dione (I; 6-Hydroxy-buspirone)

A mixture of II (4.0 g; 6.9 mmole) and 10% Pd/C (about 1 g) in MeOH (100 mL) was hydrogenated in a Parr shaker at 40–45 psi for 1 h. The hydrogenation mixture was filtered through a Celite pad which was then washed with EtOAc. The filtrate was evaporated to a gum which was purified by flash chromatography through a silica gel column eluting with EtOAc to give 0.41 g of an off-white solid (I).

Anal. Calcd. for $C_{21}H_{31}N_5O_3$: C, 62.82; H, 7.78; N, 17.44. Found: C, 62,84; H, 7.81; N, 17.33.

EXAMPLE 2

Enantiomeric Separation

Preparative Chiral HPLC Purification Procedure for 6-hydroxy-buspirone 1.1 g 6-Hydroxy-buspirone is dissolved in 55mL HPLC grade methanol (20 mg/mL). Repetitive 0.5 mL injections of the solution are made on a Chirobiotic-Vancomycin Chiral HPLC column, 22.1 mm×250 mm,10 um particle size (Advanced Separation Technologies, Inc., Whippany, N.J.) equilibrated with a mobile phase of MeOH/acetic acid/triethylamine, 100/0.2/0.1, v/v/v, at a flow rate of 20 mL/minute. The UV trace is monitored at 236 nm. Each enantiomer (RTs ~10.9 minutes for the (R)- form and ~13.4 minutes for the (S)- form, respectively) is collected in ~1000 mL of mobile phase and condensed separately under reduced pressure at 40° C. ~2 mL of clear solution resulting from the evaporation of methanol is diluted with 5 mL of $H_2O$. The pH of these solutions is adjusted from 5 to ~8 with $NH_4OH$, upon which a white precipitate is observed. The precipitates are centrifuged, and the aqueous layers extracted three times with equal volumes of methylene chloride. The methylene chloride layers are evaporated and any remaining solid is re-chromatographed. The centrifuged precipitates are washed three times with $H_2O$ to remove any residual salts and air dried at room temperature.

The basic form of each enantiomer can be converted to the hydrochloride salt by treatment of an ethanol solution of the enantiomer with ethanolic HCl.

EXAMPLE 3

One-Step Synthesis of 6-Hydroxy-buspirone (I)

Buspirone (19.3 g, 50 mmole) was dissolved in dry THF (400 mL) and the resulting solution was cooled to −78° C. A solution of $KN(SiMe_3)_2$ in toluene (100 mL, 1 M) was added slowly. After the reaction mixture was stirred at −78° C. for 1 h, a solution of 2-(phenylsulfonyl)-3-phenyloxaziridine (Davis reagent, prepared according to literature method: F. A. Davis, et al., Org. Synth., 1988, 66, 203) (17.0 g, 65 mmole) in dry THF (150 mL, precooled to −78° C.) was added quickly via a cannular. After stirred for 30 min at −78° C., the reaction was quenched with 1 N HCl solution (500 mL). It was extracted with EtOAc (3×500 mL). The aqueous layer was separated, neutralized with saturated sodium bicarbonate solution , and extracted with EtOAc (3×500 mL). The combined organic extracts were dried over $Na_2SO_4$, filtered, and concentrated under reduced pressure to give a white solid residue which was subjected to column chromatography using $CH_2Cl_2$/MeOH/$NH_4OH$ (200:10:1) as the eluent to give pure 6-hydroxy-buspirone (I, 7.2 g) and a mixture of buspirone and 6-hydroxy-buspirone (I). The mixture was purified by above column chromatography to afford another 3.3 g of pure 6-hydroxy-buspirone (I).

$^1$H NMR (CDCl$_3$) δ8.30 (d, J=4.7 Hz, 2 H), 6.48 (t, J=4.7 Hz,1 H), 4.20 (s, 1H), 3.83–3.72 (m, 5H), 3.55 (s, 1 H), 2.80 (d, J=17.5 Hz, 1H), 2.55–2.40 (m, 7H), 2.09–2.03 (m, 1H), 1.76–1.54 (m,10H), 1.41–1.36 (m, 1H), 1.23–1.20 (m, 1H).

EXAMPLE 4

Preparation of 3-Hydroxygepirone

A. 4,4-Dimethyl-3-(4-nitrobenzyloxycarbonyloxy)-1-[4-[4-(2-pyrimidinyl)-1-piperazinyl]butyl]-2,6-piperidinedione (II)

To a solution of 4-dimethyl-1-[4-[4-(2-pyrimidinyl)-1-piperazinyl]butyl]-2,6-piperidinedione (gepirone: 12.7 g, 356 mmole) in dry THF (200 mL) was added LiN (Me$_3$Si)$_2$ (37.3 mL of a 1 M THF solution) at −78° C. and the mixture was stirred for 2.5 h. A solution of di-4-nitrobenzyl peroxydicarbonate (III, 15 g) in dry THF (100 mL) was then added dropwise over 1 h. Stirring was continued at −78° C. for an additional 2 h.

The cooling bath was then removed and the reaction solution was poured into a mixture of $H_2O$ and EtOAc. The organic phase was separated and washed with $H_2O$ and then with brine. The organic phase was dried and then evaporated to a brown gum. Flash chromatography of the gum, eluting the silica gel column with EtOAc, gave crude product which was titurated in hexane to provide 7.5 g (58%) product (II) with recovery of 2.5 g of gepirone after elution of the column with acetone.

B. 4,4-Dimethyl-3-hydroxy-1-[4-[4-(2-pyrimidinyl)-1-piperazinyl]butyl]-2,6-piperidinedione (I; 3-hydroxygepirone)

A mixture of II (7.0 g; 12.6 mmole) and 10% Pd/C (3.5 g) in MeOH (70 mL) was hydrogenated in a Parr shaker at 30 psi for 0.5 h. The hydrogenation mixture was filtered through a Celite pad, which was then washed with THF. The filtrate was evaporated to a gum which was solidified by trituration in ether. Filtration gave 2 g of crude product as a beige solid. The filtrate was evaporated and the residue was flash chromatographed through a silica column eluting with EtOAc to provide an additional 1 g of crude product. The crude product was combined and suspended in MeOH. A small portion of ether was added and the mixture was filtered to give 2.5 g of I (3-hydroxygepirone) as a white solid. This material was recrystallized (acetone-hexane) to give a solid mp 122–124° C. (gas evolution).

Anal. Calcd. for $C_{19}H_{29}N_5O_3 \cdot 0.2\ H_2O$: C, 60.20; H, 7.81; N, 18.47.

Found: C, 60.21; H, 7.79; N, 18.32.

The racemic mixture of 3-hydroxygepirone can be separated into its individual enantiomers using the procedure of Example 2 or other methods of enantiomeric separation and purification known to those skilled in the art.

Pharmaceutical kits or packaging containing separate unit dosage forms of hydroxyazapirone and acetaminophen are another aspect of the present invention. Acetaminophen and hydroxyazapirone dosage forms constituting the combination are packed separately but packaged together as in kit form. Preferably the hydroxyazapirone and acetaminophen dosage forms are intended for the same route of administration and are to be given concurrently.

Most preferably, solid oral dosage formulations of each component are contained in packaging materials which protect the formulations from moisture and light. For example, suitable packaging materials include amber colored high density polyethylene bottles, amber colored glass bottles, and other containers made of a material which inhibits the passage of light. Most preferably, the packaging will include a desiccant pack. The container may be sealed with an aluminum foil blister to provide the desired protection and maintain product stability.

All the above-mentioned embodiments of concurrent administration of the acetaminophen and hydroxyazapirone components are intended for use as an improved method of treating pain. For example, their use is suited for the treatment of articular pain, and in particular in the treatment of arthritis, rheumatoid arthritis, spondylitis, gouty arthritis, osteoarthritis, and juvenile arthritis.

These embodiments can also be used within the context of the treatment of dysmenorrhea, tendinitis, and bursitis. They can also be used in the treatment of pain symptoms of myalgia, dental pain, and migraine, in the treatment of pain of cancerous origin, and also as additional treatments for infectious and febrile states.

Finally, these embodiments can find use in the treatment of neuropathic pain, and in particular of nervous pain, herpes zoster, desafferentation (phantom member) pain, diabetic neuropathies.

Examples of acetaminophen-hydroxyazapirone combination pharmaceutical formulations are given below. These examples are intended to be instructive but not exhaustive. Those skilled in the pharmaceutical arts will readily envision alternate formulations applicable to the combination embodiment of the present invention.

| Example 5: Gelatine capsule (Size No. 1) | |
|---|---|
| Acetaminophen | 500 mg |
| 3-Hydroxygepirone HCl | 3.5 mg |
| Microcrystalline cellulose | 100 mg |
| Hydroxypropyl methyl cellulose | 10 mg for one gelatine capsule |
| Example 6: Tablet | |
| Acetaminophen | 500 mg |
| 6-Hydroxybuspirone HCl | 8 mg |
| Microcrystalline cellulose | 100 mg |
| Lactose | 100 mg |
| Hydroxypropyl methyl cellulose | 10 mg |
| Magnesium stearate | 5 mg |
| Hydroxypropyl cellulose | 50 mg for one tablet |
| Example 7: Injectable preparation | |
| Acetaminophen | 1000 mg |
| 6-Hydroxybuspirone HCl | 10 mg |
| Cysteine | 50 mg |
| PEG 400 | 30 mg |
| Ethyl alcohol | 10 mg |
| Water preparation for injection | q.s.p. 100 ml |

Various modifications of the invention in addition to those shown and described herein will be apparent to those skilled in the art in view of the foregoing description. Such modifications are within the scope of the following claims.

| Example 8: Suppository | | |
|---|---|---|
| Acetaminophen | 1000 mg | |
| 6-Hydroxygepirone HCl | 20 mg | |
| Semi-synthetic glyceride | 2000 mg | for one suppository |

EXAMPLE 9

Experimental Procedure for Rat Hindpaw Withdrawal Test for Analgesia (Acute Pain)

To assess the thermally evoked paw-withdrawal response, a commercially available device was used. Specifics of device construction and operation have been published previously (Dirig D M, Salami A, Rathbun M L, Ozaki G T, Yaksh T L. Characterization of variables defining hindpaw withdrawal latency evoked by radiant thermal stimuli. J Neurosci Methods. Oct. 3, 1997; 76(2):183–91). This device is comprised of a glass surface on which the rats were placed individually in Plexiglas cubicles (9×22×25 cm). The surface is maintained at 30° C. by a feedback-controlled, under-glass, forced-air heating system. The thermal nociceptive stimulus originates from a projection bulb below the glass that can be manipulated in a two-dimensional axis on ball bearing slides. This apparatus allows the stimulus to be delivered separately to each hind paw with the aid of an angled mirror mounted on the stimulus source. A timer is actuated with the light source, and escape latency is defined as the time between stimulus onset and the display of a brisk paw withdrawal (detected by photodiode motion sensors that stops the timer and terminates the stimulus; cut-off time for a non-response is 20 sec which triggers automatic termination of the stimulus). In the present study, animals are placed in test boxes for 30 min acclimation and then baseline escape latency is assessed separately for each hindpaw (left and right) at −15 min. All drugs are delivered at 0 min by the intraperitoneal (i.p.) route in a volume of 3 ml/kg. The vehicle for 6-hydroxybuspirone was 0.9% sodium chloride (Saline). For 3-hydroxygepirone the vehicle was deionized H2O plus a few drops of hydrochloric acid. For acetaminophen (Sigma, A7085) the vehicle was 40% polyethylene glycol 400 (PEG-400), 10% EtOH, 15% Tween 80, and 35% deionized H2O (PETW). Acetaminophen was dissolved sequentially in two parts: 1) first into a solution of 80% PEG 400+20% EtOH, and 2) then slowly added to it was an equal volume of 30% Tween 80+70% deionized H2O (sonicated as needed). Each animal received two injections at time zero. Specifically, animals were tested in one of the following 6 treatment conditions (abbreviations used in figures are shown under "Key" below):

| Treatment | Key | Dual injection (each injected separately; 3 ml/kg; ip) |
|---|---|---|
| 1) | saline + PETW | Saline + PETW |
| 2) | 6-OH-Busp 5 mg/kg | 6-OH-buspirone (5 mg/kg) + PETW |
| 3) | 3-OH-Gep 5 mg/kg | 3-OH-gepirone (5 mg/kg) + PETW |
| 4) | Acet 300 mg/kg | Acetaminophen (300 mg/kg) + Saline |
| 5) | 6-OH-Busp + Acet, 5 + 300 mg/kg | 6-OH-buspirone (5 mg/kg) + acetaminophen (300 mg/kg) |
| 6) | 3-OH-Gep + Acet, 5 + 300 mg/kg | 3-OH-gepirone (5 mg/kg) + acetaminophen (300 mg/kg) |

Following drug administration, thermal escape latencies are measured at 15, 30, 60, 90 and 120 min (mean of both paws is used for statistical analysis).

What is claimed is:

1. A method for the treatment of pain by the concurrent administration of acetaminophen and a pain-relief enhancing amount of a hydroxyazapirone selected from the group consisting of 6-hydroxybuspirone and 3-hydroxygepirone or a pharmaceutically acceptable salt or solvate thereof.

2. The method of claim 1 wherein the hydroxyazapirone is 6-hydroxybuspirone.

3. The method of claim 1 wherein the hydroxyazapirone is 6-hydroxygepirone.

4. The method of claim 2 wherein the 6-hydroxybuspirone is in the form of one of its enantiomers substantially free of the other enantiomer.

5. The method of claim 3 wherein the 3-hydroxygepirone is in the form of one of its enantiomers substantially free of the other enantiomer.

6. The method of claim 1 wherein an HCl salt is the pharmaceutically acceptable salt of the azapirone.

7. The method of claim 1 wherein acetaminophen and the hydroxyazapirone are administered separately.

8. The method of claim 1 wherein acetaminophen and the hydroxyazapirone are administered in combination.

9. The method of claim 1 wherein at least 200 to 1300 mg of acetaminophen and at least 0.5 to 20 mg of the hydroxyazapirone or an acid salt form thereof are administered.

10. A pharmaceutical composition comprising a therapeutically effective amount of acetaminophen and a pain-relief enhancing amount of a hydroxyazapirone selected from 6-hydroxybuspirone or 3-hydroxygepirone or a pharmaceutically acceptable salt thereof.

11. The composition of claim 10 in which the weight ratio of hydroxyazapirone to acetaminophen is from 1:10 to 1:2600.

12. The composition of claim 10 in which the weight ratio of hydroxyazapirone to acetaminophen is from 1:30 to 1:650.

13. The composition of claim 10 in which the weight ratio of hydroxyazapirone to acetaminophen is from 1:40 to 1:150.

14. The pharmaceutical composition of claim 6 wherein an HCl salt is the pharmaceutically acceptable salt of the hydroxyazapirone.

15. The pharmaceutical composition of claim 10 in unit dose form.

16. A pharmaceutical kit package containing therapeutically effective dosage forms of acetaminophen and effective pain-relief enhancing dosage forms of a hydroxyazapirone selected from 6-hydroxybuspirone and 3-hydroxygepirone.

17. The pharmaceutical composition of claim 10 in a formulation suitable for oral administration.

18. The pharmaceutical formulation of claim 17 wherein the hydroxyazapirone is 6-hydroxybuspirone HCl.

19. The pharmaceutical composition of claim 17 wherein the hydroxyazapirone is 3-hydroxygepirone HCl.

20. The pharmaceutical composition of claim 10 in a formulation suitable for parenteral administration.

21. The pharmaceutical composition of claim 10 in a formulation suitable for buccal administration.

22. The pharmaceutical composition of claim 10 in a formulation suitable for rectal administration.

* * * * *